(12) United States Patent
Kealey et al.

(10) Patent No.: US 12,285,346 B2
(45) Date of Patent: Apr. 29, 2025

(54) THIN-FILM MICROMESH AND RELATED METHODS

(71) Applicant: Monarch Biosciences, Inc., Los Angeles, CA (US)

(72) Inventors: Colin Kealey, Los Angeles, CA (US); Vikas Gupta, Los Angeles, CA (US)

(73) Assignee: MONARCH BIOSCIENCES, INC., Los Angeles, CA (US)

( * ) Notice: Subject to any disclaimer, the term of this patent is extended or adjusted under 35 U.S.C. 154(b) by 915 days.

(21) Appl. No.: 17/203,349

(22) Filed: Mar. 16, 2021

(65) Prior Publication Data

US 2021/0196489 A1    Jul. 1, 2021

Related U.S. Application Data

(63) Continuation of application No. 16/048,136, filed on Jul. 27, 2018, now Pat. No. 10,945,868.

(51) Int. Cl.
*A61F 2/915* (2013.01)
*A61F 2/82* (2013.01)

(52) U.S. Cl.
CPC ........ *A61F 2/915* (2013.01); *A61F 2002/823* (2013.01); *A61F 2002/825* (2013.01); *A61F 2002/91541* (2013.01); *A61F 2002/91575* (2013.01); *A61F 2210/0014* (2013.01); *A61F 2230/0069* (2013.01); *A61F 2240/001* (2013.01)

(58) Field of Classification Search
CPC ............... A61F 2/915; A61F 2002/823; A61F 2002/825; A61F 2002/91541; A61F 2002/91575; A61F 2210/0014; A61F 2230/0069; A61F 2/88; A61F 2002/91558
See application file for complete search history.

(56) References Cited

U.S. PATENT DOCUMENTS 7,704,274 B2 * 4/2010 Boyle ................... C23C 14/165
623/1.13

\* cited by examiner

*Primary Examiner* — Elizabeth Houston
*Assistant Examiner* — David P Stein
(74) *Attorney, Agent, or Firm* — Haynes and Boone, LLP (57) ABSTRACT

Thin-film mesh for medical devices and related methods are provided. The thin-film mesh may include slits to be expanded into pores, and the expanded thin-film mesh may be used as a cover for a stent device. The thin-film mesh has a tube-shape and the slits may be angled with respect to a longitudinal axis of the tube-shape thin-film mesh. The angled slits allow for the thin-film mesh to expand in multiple dimensions, including along the longitudinal axis and along the circumferential direction of the tube-shape thin-film mesh. The slits may be provided in diagonal rows arranged in longitudinal columns. Longitudinal columns of different types of slits may be arranged along the circumferential direction on the tube-shape thin-film mesh to form a zig-zag pattern of slits. The thin-film mesh may be formed from thin-film Nitinol (TFN) and may be fabricated via sputter deposition on a micropatterned wafer.

20 Claims, 11 Drawing Sheets

THIN-FILM MICROMESH AND RELATED METHODS

CROSS-REFERENCE TO RELATED APPLICATION

This application is a Continuation application of, and claims priority to and the benefit of, U.S. patent application Ser. No. 16/048,136, filed Jul. 27, 2018, the entire disclosure of which is expressly incorporated by reference herein.

TECHNICAL FIELD

The present disclosure generally relates to medical devices and, more particularly, to thin-film micromeshes and related methods.

BACKGROUND

A conventional endovascular stent typically is a braided wire device that is compressed and delivered using a catheter and guide wire to a treatment location inside a patient. For example, the braided wire device may divert blood flow to reduce pressure on an aneurysm, such that the aneurysm no longer poses imminent danger of rupture to the patient.

A thin-film micromesh may be used to cover the endovascular stent. The stent may be deployed in tortuous neurovascular beds and may under undergo dramatic changes in the radial and axial dimensions during the delivery and implantation process. Accordingly, there is a need in the art for an improved thin-film micromesh that allows for flexibility in multiple dimensions.

Embodiments of the present disclosure and their advantages are best understood by referring to the detailed description that follows. It should be appreciated that like reference numerals are used to identify like elements illustrated in one or more of the figures, in which the showings therein are for purposes of illustrating the embodiments and not for purposes of limiting them.

DETAILED DESCRIPTION

Thin-film micromeshes (also referred to as thin-film meshes) with multiple axes of expansion and related methods are provided. In particular, a thin-film micromesh may include one or more slits or fenestrations arranged or orientated to form an angle with a longitudinal direction of a cylindrical-shape thin-film mesh device. For example, the slits or fenestrations may extend or be elongated in an angled directions with respect to the longitudinal direction of the cylindrical-shape thin-film mesh device. The angled slits or fenestrations may allow the thin-film micromesh to expand in multiple dimensions, such as in radial directions and longitudinal directions of the cylindrical-shape thin-film mesh device. Thus, the angled slits or fenestrations allow the thin-film micromesh to be expandable and flexible in multiple dimensions.

As used herein, a thin-film mesh may be less than 100 μm (micrometers or microns) in thickness. In various embodiments, a thin-film mesh may be formed using fenestrated thin-film Nitinol (TFN). Other thin-film mesh materials may be used to form the thin-film mesh disclosed herein. The following discussion is thus directed to TFN meshes without loss of generality.

Figure 1A:
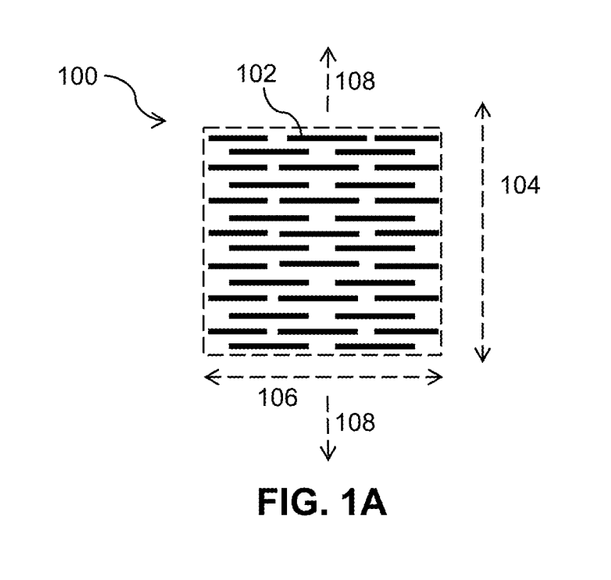
FIG. 1A is a diagrammatic top plan view of a portion of a thin-film micromesh before expansion according to an embodiment.
Figure 1B:
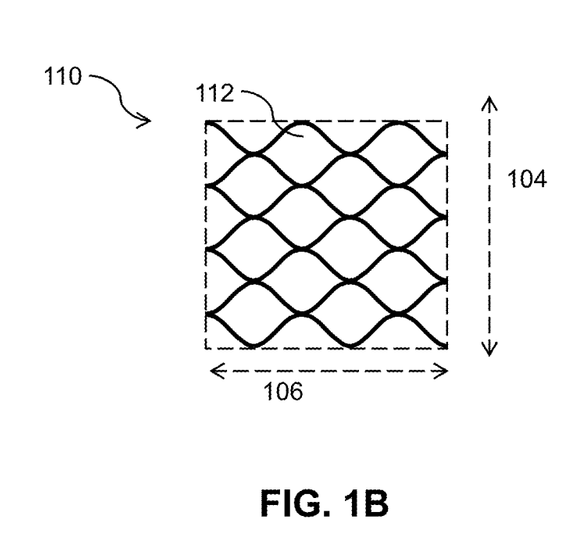
FIG. 1B is a diagrammatic top plan views of a portion of a thin-film micromesh after expansion according to an embodiment.
Figure 1C:
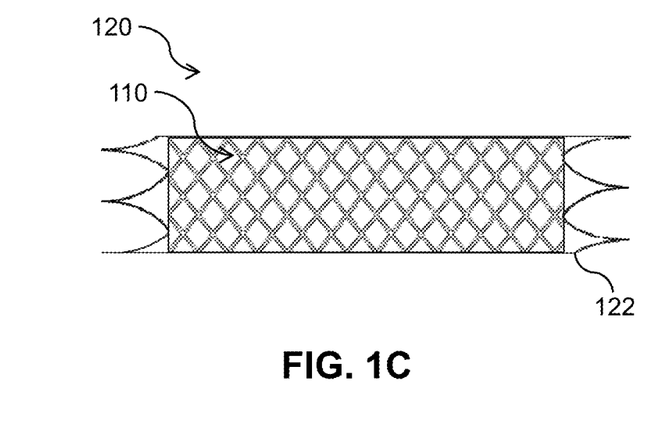
FIG. 1C is a diagrammatic perspective side view of a thin-film micromesh device according to an embodiment.
Figure 1D:
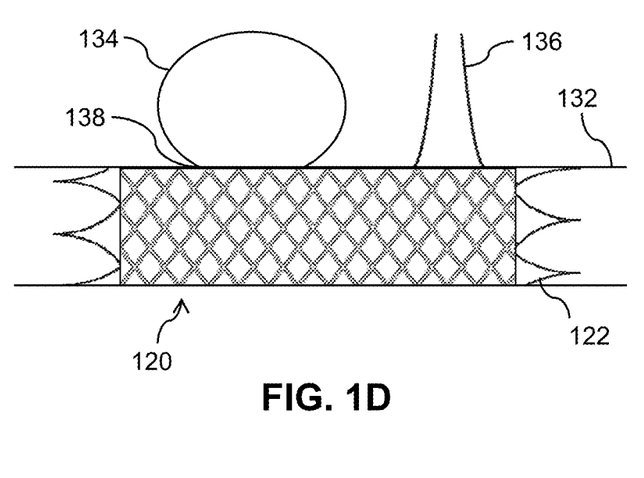
FIG. 1D is a diagrammatic cross-sectional view of a blood vessel with an aneurysm in which a thin-film micromesh device is placed according to an embodiment.

FIGS. 1A-E show a thin-film mesh 100, 110 and a thin-film mesh device 120, a medical device including thin-film mesh 110. FIG. 1A is a diagrammatic top plan view of a portion of thin-film mesh 100 with slits 102 (e.g., closed fenestrations) prior to expansion. The slits 102 may be elongated or extend parallel to axis 106. As such, thin-film mesh 100 may be expanded along axis 104, which may be referred to as axis of expansion 104, to open up slits/fenestrations 102. In particular, slits/fenestrations 102 may be oriented perpendicular to axis 104 and parallel to axis 106, which may be referred to as slit axis 106. Thin-film mesh 100 may be extended in directions 108 to form thin-film mesh 110, as shown in FIGS. 1B, 1C and 1D.

FIG. 1B is a diagrammatic top plan view of a portion of thin-film mesh 110 including pores 112 (e.g., open fenestrations) after expansion. Thin-film mesh 110 may be formed by expanding thin-film mesh 100 in FIG. 1A. The expansion may extend thin-film mesh 100 along axis 104 such that there is a large increase in length along axis 104 but a small change (e.g., a small decrease) in length along axis 106. In some embodiments, the expansion may extend thin-film mesh 100 along axis 104 in a range from 50% to 800%.

When expanded, slits/fenestrations 102 in FIG. 1A open up into pores/fenestrations 112 to form a "chain-link" fence pattern, such as diamond-shaped pores/fenestrations. Thin-film mesh 110 forms struts around each diamond-shaped pore/fenestration 112. Alternatively, thin-film mesh 110 may be directly formed with diamond-shaped pores 112 (e.g., in its final configuration or partially opened). It will be appreciated that other pore/fenestration shapes may be used in other embodiments.

Thin-film mesh 110 may be formed, for example, as a thin-film mesh cover for a stent backbone (e.g., backbone 122 in FIG. 1C and FIG. 2D) or as a thin-film mesh scaffold for tissue engineering. Thin-film mesh 110 may otherwise be included in a medical device for its advantageous properties as further described herein.

FIG. 1C is a diagrammatic perspective side view of thin-film mesh device 120 that includes thin-film mesh 110 and a backbone 122 (e.g., a stent backbone). Thin-film mesh 110 expanded to its three-dimensional form (e.g., a cylindrical tube or other shape) may be assembled over backbone 122, which provides structural support for thin-film mesh 110 while maintaining the advantageous features of thin-film mesh 110, such as fibrin deposition and cell growth (e.g., endothelialization) when placed in a blood vessel.

FIG. 1D shows a diagrammatic cross-sectional view of a blood vessel 132 with an aneurysm 134 and a branch vessel 136 (e.g., a branch artery) in which thin-film mesh device 120 of FIG. 1C is implanted. Thin-film mesh device 120 may advantageously be used as a flow diverter due to the properties of thin-film mesh 110. Flow diverters may be required to strike a balance between diverting flow from an aneurysm sac while permitting flow in any perianeurysmal branch vessels. Thin-film mesh 110 advantageously diverts blood flow into aneurysm 134 and promotes rapid deposition of fibrin and endothelialization at a neck 138 of aneurysm 134 so that aneurysm 134 is occluded, while at the same time allowing blood flow through branch vessel 136.

Thin-film mesh device 120 advantageously has a reduced rate of delayed aneurysm rupture when compared to conventional flow diverters. Conventional wire flow diverter stents may provide occlusion of aneurysm necks, but because the pores of such devices are often filled with particles made up of blood coagulation products, inflammatory cells, and cellular debris, such particles may be dislodged and cause delayed aneurysm rupture. Indeed, endothelialization is slow to occur and is often partial at best in conventional wire flow diverter stents. In contrast, thin-film mesh 110 provides a structure on which the blood vessel walls are rapidly rebuilt through endothelialization, promoting a healthy and stable cellular lining, and because the cellular lining is not prone to dislodging particles of blood coagulation products and the like, the rate of delayed aneurysm rupture is significantly reduced.

Figure 1E:
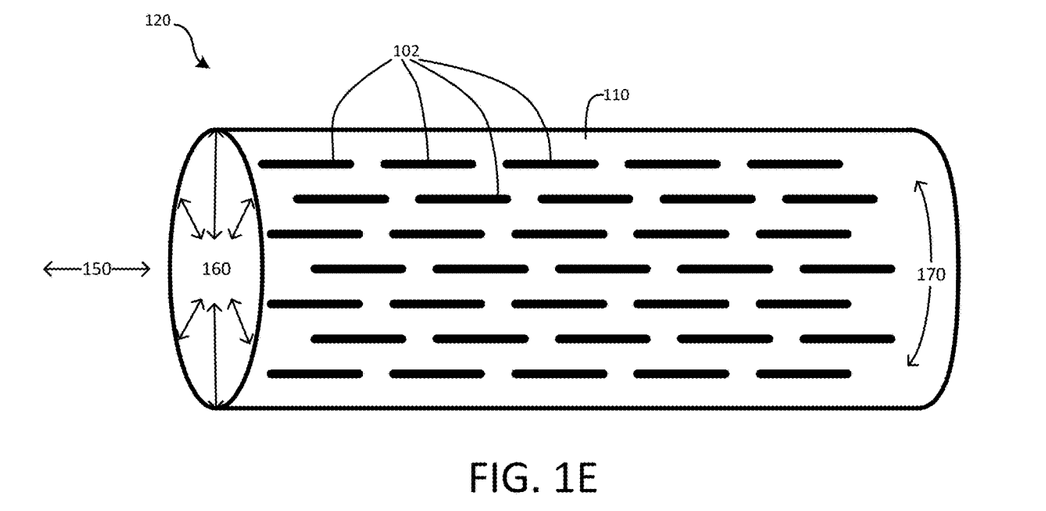
FIG. 1E is a diagrammatic perspective side view of a thin-film micromesh device with slits or fenestrations according to an embodiment.

As shown in FIG. 1E, the slits or fenestrations 102 on the thin-film mesh 110 may be arranged to extend or be elongated in a direction parallel to a longitudinal axis 150 of the cylindrical-shape thin-film mesh device 120. This arrangement allows the slits or fenestrations 102 to expand in a circumferential direction 170 of the cylindrical-shape thin-film mesh device 120. As such, the cylindrical-shape thin-film mesh 110 may expand in radial directions 160. For example, the cylindrical-shape thin-film mesh device 120 may be stored in a contracted state in which the cylindrical-shape thin-film device 120 has a relative small diameter for delivery to a treatment site inside a patient. The cylindrical-shape thin-film mesh device 120 may then be deployed to expand in radial directions 160 at the treatment site. For example, the cylindrical-shape thin-film device 120 may expand radially to have a larger diameter to press on and attach to an inner wall of a blood vessel. Thus, thin-film mesh 110 with slits or fenestrations 120 that extend along a direction parallel to the longitudinal axis 150 of the cylindrical-shape thin-film device 120 allows for expansion in radial directions 160.

However, such slit or fenestration arrangement results in limited expansion or flexibility in the longitudinal direction 150 of the cylindrical-shape thin-film device 120. For example, the thin-film device 120 may be deployed in tortuous neurovascular beds and may undergo dramatic changes in both radial and longitudinal dimensions during the delivery and implantation process.

Figure 1F:
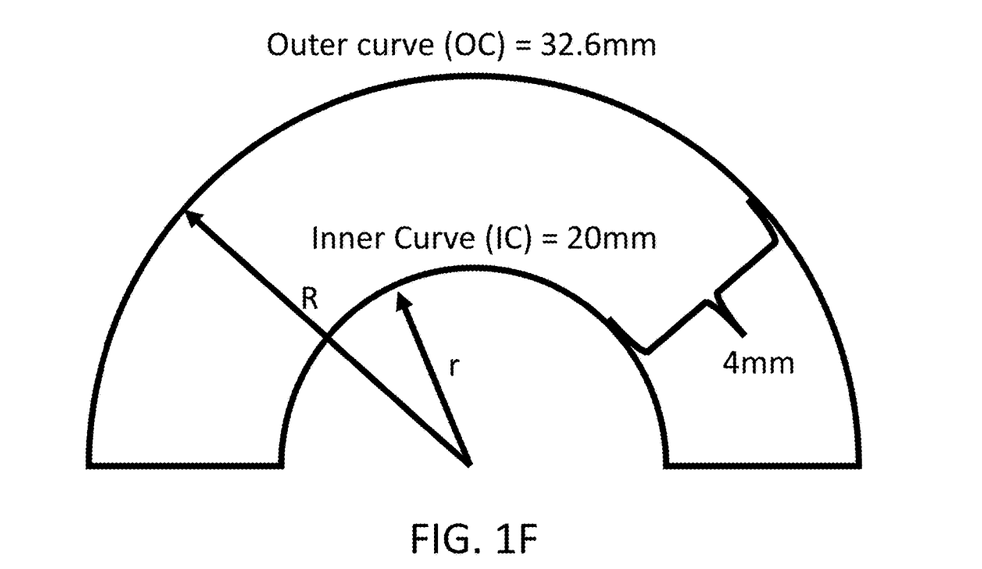
FIG. 1F illustrates a scenario in which a thin-film micromesh device is contoured or bent according to an embodiment.

FIG. 1F illustrates a scenario in which the cylindrical-shape thin-film device 120 is contoured or bent into a U shape. The U-shape may be required to conform to a particular treatment location in a patient. The inner radius r of the U-shape may be about 6.37 mm, the outer radius R of the U-shape may be about 10.37 m, and the diameter of the cylindrical-shape thin film device 120 may be about 4 mm. In such scenario, the outer curve (about 32.6 mm) may be about 63% longer than the inner curve (about 20 mm). To conform to such treatment location, the outer curve side of the cylindrical-shape thin-film device 120 would have to expand about 63% more than the inner curve side along the longitudinal direction 150 of the cylindrical-shape thin-film device 120. Thus, the cylindrical-shape thin-film device 120 that expands mainly in the radial directions and has limited expandability or flexibility in the longitudinal direction may not meet such requirements.

Accordingly, an improved thin-film micromesh that allows for flexibility in multiple dimensions is proposed. For example, the improved thin-film micromesh may have slits or fenestrations that are arranged to extend or be elongated in a direction that forms an angle with a longitudinal axis of a cylindrical-shape thin-film device. In particular, the angled slits or fenestrations may allow the thin-film micromesh to expand both in the radial directions and along the longitudinal axis of the cylindrical-shape thin film device.

Figure 2A:
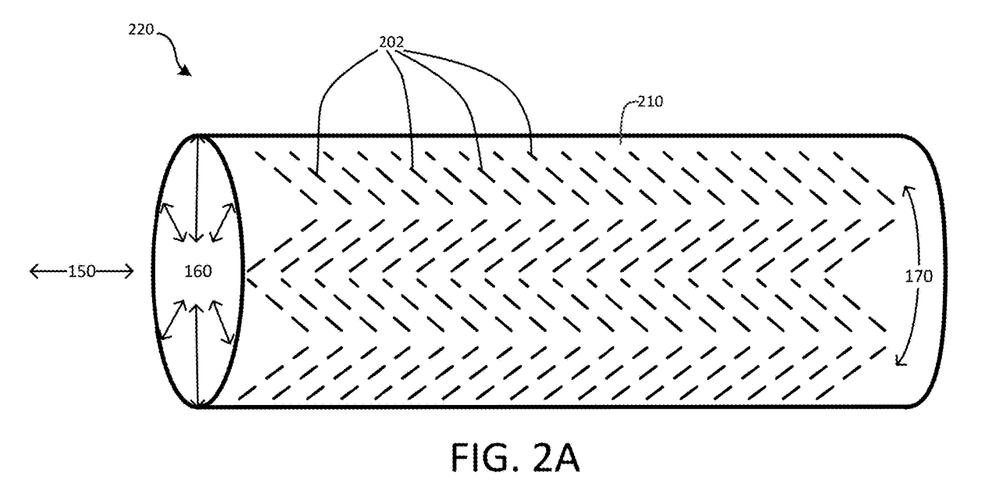
FIG. 2A is a diagrammatic perspective side view of a thin-film micromesh device with angled slits or fenestrations according to an embodiment.

FIG. 2A illustrates a perspective view of a thin-film mesh device 220 provided with an improved thin-film mesh 210 that allows for flexibility and expansion in multiple dimensions. Thin-film mesh 210 may include a plurality of angled slits or fenestrations 202. In particular, slits or fenestrations 202 may be elongated or may extend in directions that form angles (e.g., not parallel) with the longitudinal axis 150 of cylindrical-shape thin-film mesh device 220. The angled slits or fenestration allow thin-film mesh 210 to expand in a circumferential direction 170 of cylindrical-shape thin-film mesh device 220. Such circumferential expansion allows the cylindrical-shape thin-film mesh device 220 to expand in radial directions 160. The angled slits or fenestration also allow thin-film mesh 210 to expand along the longitudinal axis 150 of the thin-film mesh device 220. Expansion in the longitudinal axis 150 allows the thin-film mesh device 220 to be flexible along the longitudinal axis 150, such that the thin-film mesh device 220 may bend or contour during the delivery process and conform to various shapes of treatment locations in patients.

Figure 2B:
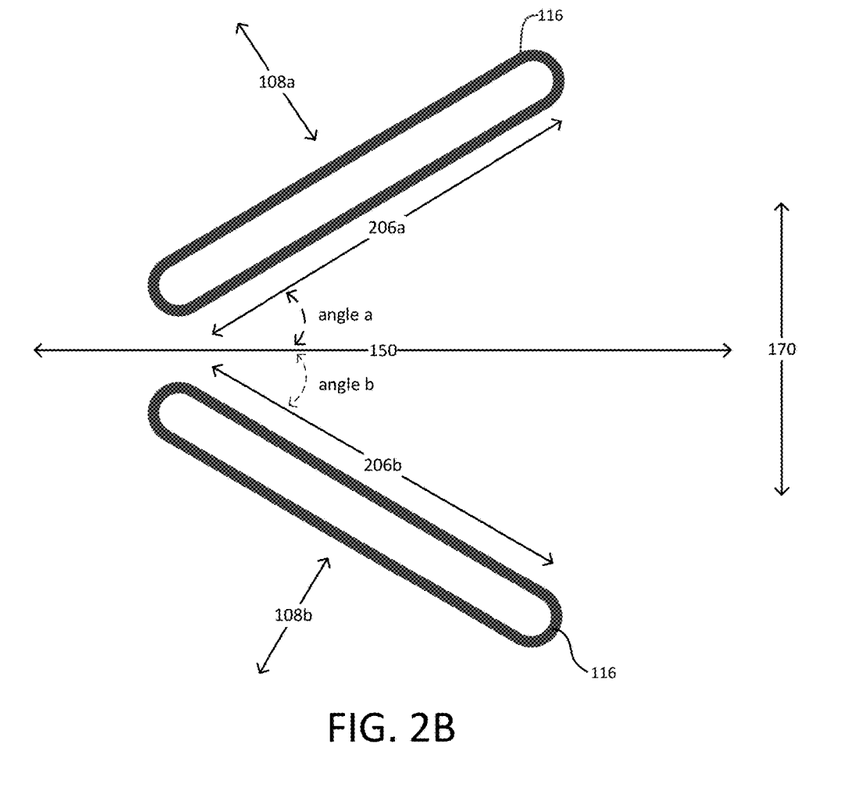
FIG. 2B illustrates angled slits or fenestrations on a thin-film micromesh according to an embodiment.

FIG. 2B illustrates different types of angled slits or fenestrations in a thin-film mesh. For example, thin-film mesh 210 may have at least two different types of slits or fenestrations 202a and 202b. Each of the fenestrations or slits 202a and 202b may be surrounded and formed by corresponding struts 116. For example, the fenestrations or slits 202a and 202b may each have an elongated oval shape including semicircles on two ends and two parallel sides. Other shapes of slits or fenestrations may be used based on the particular application of the thin-film mesh device 220.

Surrounding struts 116 may have a strut width between 1 and 25 µm. Each of slits/fenestrations 202a and 202b may have a slit length of between 25 µm and 500 µm. Different types of slits or fenestrations may have different slit dimensions, such as different lengths, widths, shapes, and the like. For example, the slit lengths may be modulated based on the type of medical device, the type of medical treatment, the body region being treated, and/or the type of aneurysm being treated. In some embodiments, the slit lengths of slits 202a and 202b may be between 50 µm and 300 µm (e.g., between 50 µm and 225 µm, or between 50 µm and 200 µm) to provide thin-film mesh device 220 with advantageous features such as fibrin deposition and cell growth (e.g., endothelialization) when placed in a blood vessel.

Slit 202a may extend or be elongated along a slit axis 206a. As shown in FIG. 2B, slit axis 206a may form an angle a with the longitudinal axis 150 of the cylindrical-shape thin-film mesh device 220. Slit 202a may expand along an expansion direction 108a. Expansion direction 108a may be perpendicular to the slit axis 206a. Thus, slit 202a may be expanded diagonally in the expansion direction 108a, which has vector components in both the circumferential direction 170 and the longitudinal direction 150. As such, the diagonally expanding slit 202a may allow thin film mesh 210 to expand in both the circumferential direction 170 and the longitudinal direction 150.

As the angle a increases, the vector components of the expansion direction 108a increases along the longitudinal direction 150 and decreases in the circumferential direction 170. Thus, the slit 202a may become more expandable in the longitudinal direction 150 and less expandable in the circumferential direction 170. As the angle a decreases, the vector components of the expansion direction 108a decreases along the longitudinal direction 150 and increases in the circumferential direction 170. As such, the slit 202a may become more expandable in the circumferential direction 170 and less expandable in the longitudinal direction. Thus, the angle a of slit 202a may be determined and adjusted based on the particular application and use for the thin film micromesh 210 (e.g., radial expandability v. longitudinal expandability).

Similarly, slit 202b may extend or be elongated along a slit axis 206b, which forms an angle b with the longitudinal axis 150 of the cylindrical-shape thin film mesh device 220. Slit 202b may expand along an expansion direction 108b, which is perpendicular to the slit axis 206b. Thus, similar to slit 202a, slit 202b also allows for diagonal expansion of thin film mesh 210, but they have different diagonal expansion directions.

In some embodiments, slit 202a and slit 202b may complement each other. For example, slits 202a and 202b may be angled from the longitudinal axis 150 by the same amount (e.g., angle a=angle b), but in opposite directions. As shown in FIG. 2B, slits 202a and 202b may be mirror image of each other with respect to the longitudinal axis 150. Slits that are different but complement each other in this manner may allow for symmetrical and/or uniform expansion of thin film micromesh 210. This may prevent undesired wrinkles or ripples in the thin film micromesh 210 when expanded.

Figure 2C:
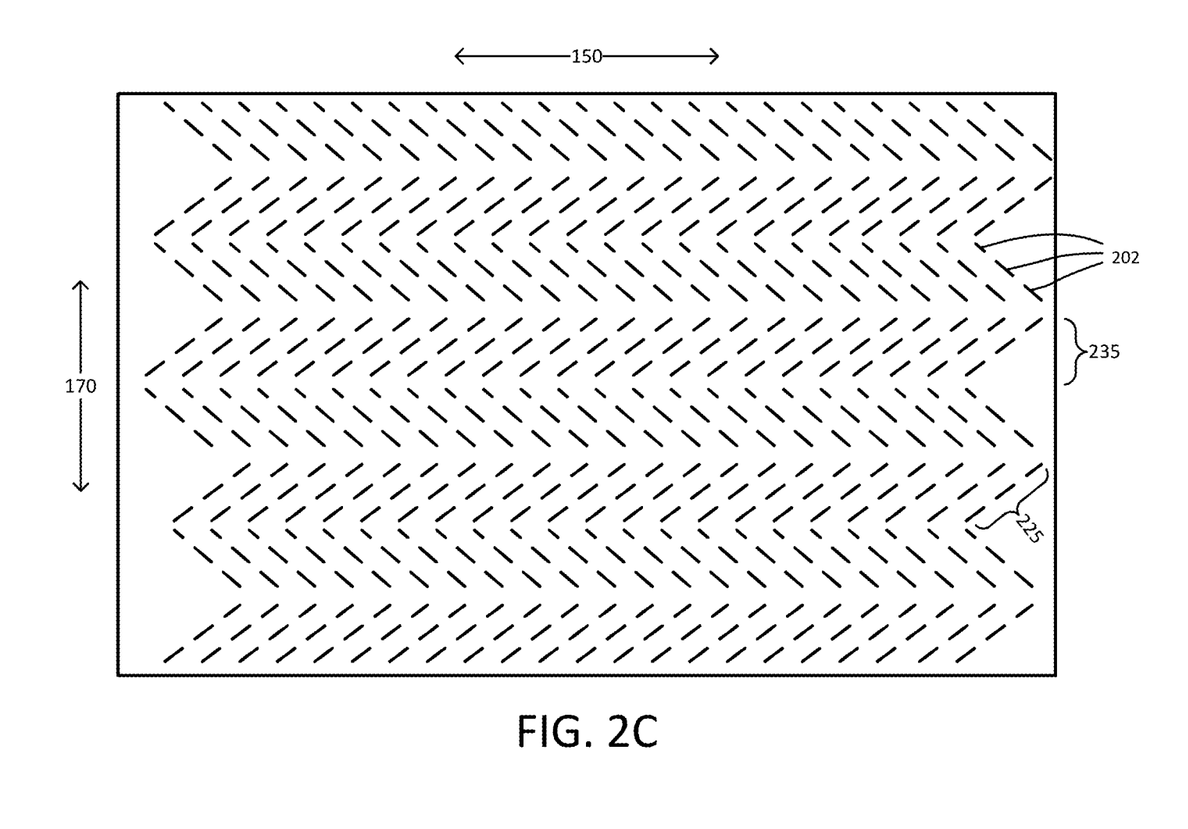
FIG. 2C is a diagrammatic top plan view of a portion of a thin-film micromesh with angled slits or fenestrations according to an embodiment.

As shown in FIG. 2C, different types of slits or fenestrations 202 with different orientations and arrangements may be provided on the thin film mesh 210. Slits or fenestrations with the same orientation may be grouped together in rows and columns. For example, slits with the same angles may line up in a diagonal row 225. As such, slits 202 arranged in the same diagonal row 225 have the same slit axis, which forms the same angle with the longitudinal axis 150. Diagonal rows 225 of the same slits may be arranged in parallel to each other to form a longitudinal column 235. Different types of slits 202 may be arranged in different longitudinal columns 235 in thin-film micro mesh 210.

Figure 2D:
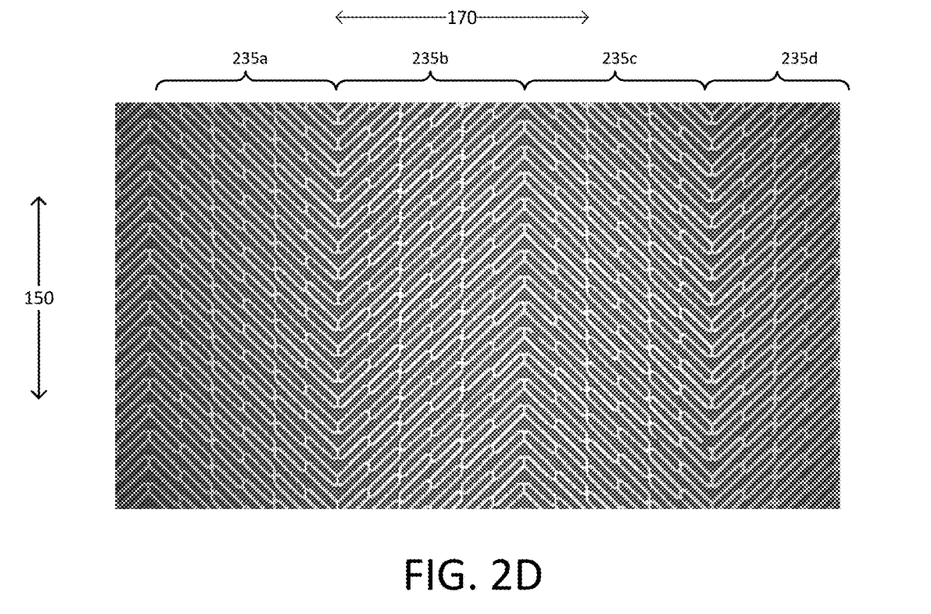
FIG. 2D is an image of a portion of a thin-film micromesh with angled slits or fenestrations according to an embodiment.

As shown in FIG. 2D, a first type of slits may be provided in first type longitudinal columns 235a and 235c and a second type of slits may be provided in second type longitudinal columns 235b and 235d. The first type longitudinal columns 235a and 235c and the second type longitudinal columns 235b and 235d may be arranged to alternate in the circumferential direction 170. For example, a first type longitudinal column 253b is provided between two adjacent second type longitudinal columns 235a and 235c. This provides a zig-zag pattern of slits between different longitudinal columns. In some embodiments, the longitudinal columns may have the same width and the slits 202 of adjacent longitudinal columns may complement each other (e.g., mirror image of each other). This provides symmetrical and/or even expansion of the thin film micromesh 210, which prevents undesired wrinkles or ripples in the thin film micromesh 210.

Figure 2E:
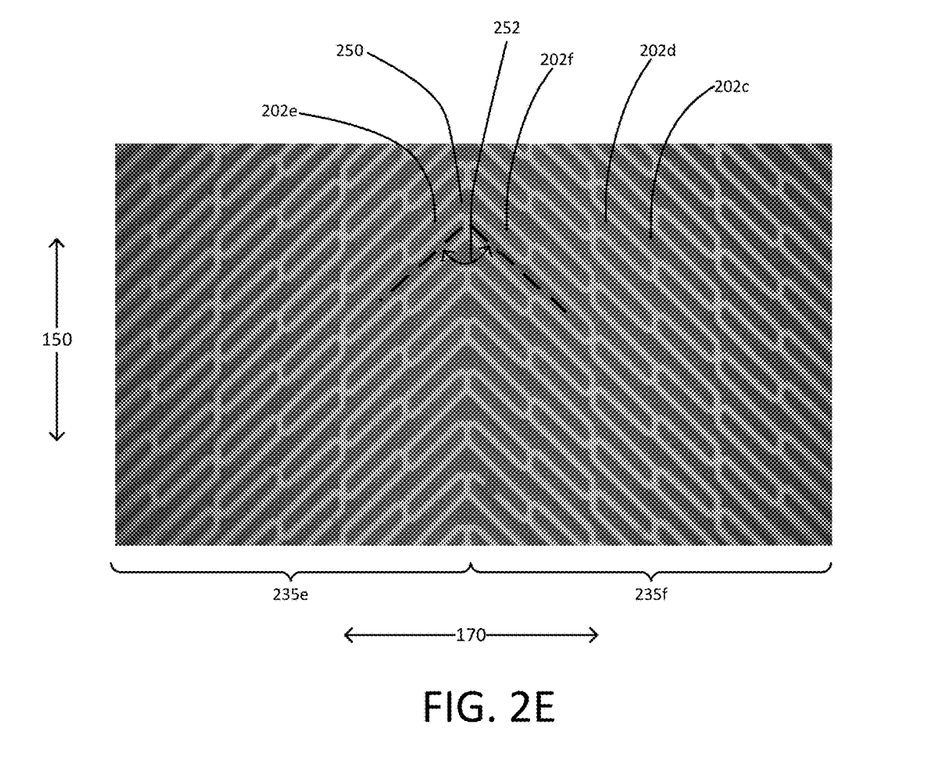
FIG. 2E is a close-up image of a portion of a thin-film micromesh according to an embodiment.

FIG. 2E illustrates a close-up view of a portion of the thin-film micro mesh 210. Slits 202 may be formed by surrounding struts 116. For example, struts 116 may form diagonal rows of slits 202. Slits 202 of adjacent diagonal rows may be staggered in an overlapping manner. For example, as shown in FIG. 2E, slit 202c may be staggered from slit 202d in the adjacent diagonal row. Staggering slits 202 in adjacent diagonal rows may provide an overall chain link pattern in the thin film micro mesh 210 that allows the thin-film micro mesh 210 to expand effectively.

Adjacent longitudinal columns 235 may have different types of slits 202. For example, as shown in FIG. 2E, longitudinal column 235e has slits 202 that angled differently from slits in longitudinal column 235f V-shaped slits 250 may be formed between two different types of longitudinal columns 235e and 235f. A V-shaped slit 250 may be formed by portions of two different types of slits 202e and 202f. An angle 252 may be formed between the slit axes of the two different types of slits 202e and 202f. The angle 252 may determine the expandability of the thin-film micromesh 210 to in the circumferential direction 170 as compared to the longitudinal direction 150. For example, a larger angle 252 may increase the expandability of the thin film micromesh 210 in the longitudinal direction 150 while decrease the expandability of thin film micromesh 210 in the circumferential direction 170. A smaller angle 252 may decrease the expandability of thin film micromesh 210 in the longitudinal axis 150 while increase the expandability of the thin film micromesh 210 in the circumferential direction 170. The angle 252 may be determined and adjusted based on the particular application and use for the thin film micromesh 210.

Further, the ability of thin-film mesh 210 to effectively expand may depend on the lengths of slits 202. Slits 202 with longer slit lengths have greater ability for expansion, while slits 202 with a shorter slit length have less ability for expansion. The dimension of slits 202 also may define the pore density of the thin film mesh micro 210. In some embodiments, thin-film mesh 210 has a pore density (fenestrations per square mm) of between 15 pores/mm$^2$ and 2217 pores/mm$^2$, and a percent metal coverage (PMC) of between 6% and 83%. In some embodiments, thin film mesh 210 has a high pore density (e.g., 50 pores/mm$^2$-3000 pores/mm$^2$) and a low metal coverage (e.g., 10%-35%), which may advantageously promote a planar deposition of fibrin followed by rapid cell growth (e.g., endothelialization).

Figure 2F:
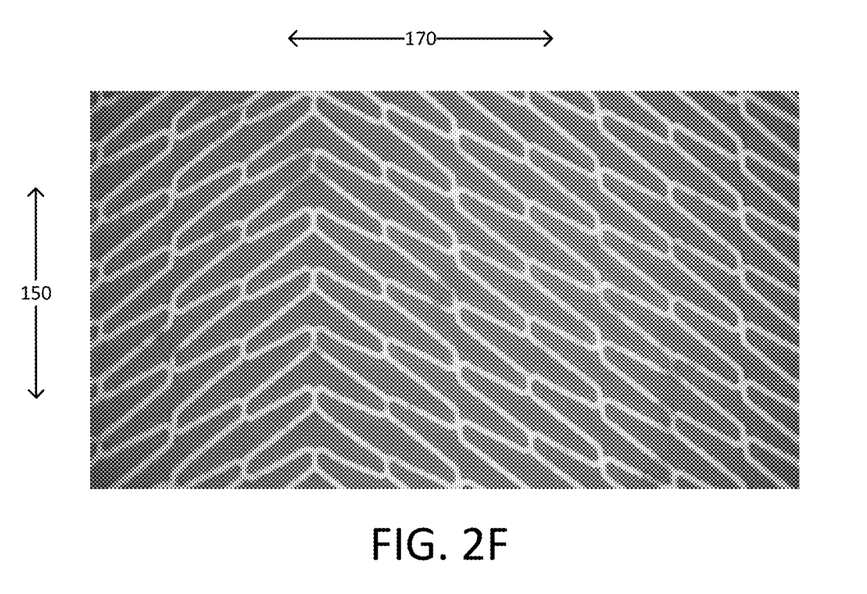
FIG. 2F is an image of a portion of thin-film micromesh stretched in a particular direction according to an embodiment.
Figure 2G:
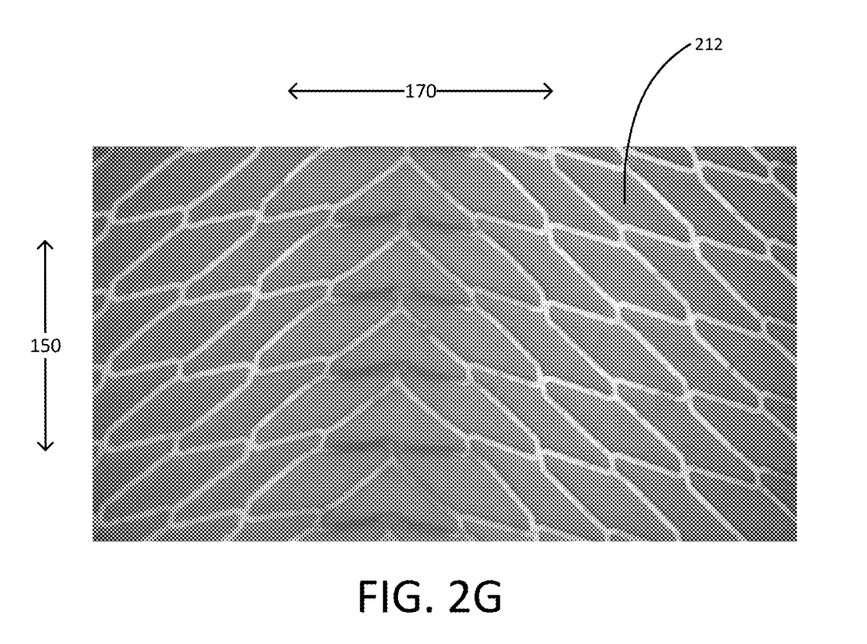
FIG. 2G is an image of a portion of thin-film micromesh stretched in another direction according to an embodiment.

FIG. 2E illustrates a thin-film micro mesh 210 in a non-expanded state. FIG. 2F illustrates that the thin-film micro mesh 210 is stretched mainly in the circumferential direction 170. The circumferential stretch may allow the thin-film micro mesh device 220 to expand in the radial directions 160. FIG. 2G illustrates that the thin-film micro mesh 210 is stretched mainly in the longitudinal direction 150 of the thin-film micro mesh device 220. The slits 202 may open up to form diamond-shaped pores 212. The longitudinal stretch may allow the thin-film micro mesh device 220 to expand and/or be flexible along the longitudinal axis 150.

The thin-film micro mesh 210 may be customized to have a particular combination of parameters based on a particular application the thin-film micro mesh 210. For example, the angle 252 (e.g., angle a+angle b) formed between slit axes may be adjusted to change the expandability of the thin-film micro mesh 210 in the circumferential direction 170 versus the longitudinal axis 150. The size and dimension of the slits 202 also may be adjusted. For example, a longer slit length may increase the expandability of the slits 202.

In some embodiments, the size of longitudinal columns and/or the number of slits in a diagonal row also may be adjusted to increase or decrease the force required to expand the micro mesh 210. For example, increasing the number of slits 202 in a diagonal row 235 may decrease the force required to expand the micro mesh 210. The width or thickness of the struts 116 also may be adjusted to increase or decrease the percentage metal in the micro mesh 210 and/or the force required to expand the micro mesh 210. For example, wider and/or thicker struts 116 may increase the percentage metal and/or increase the force required for expansion.

Figure 3:
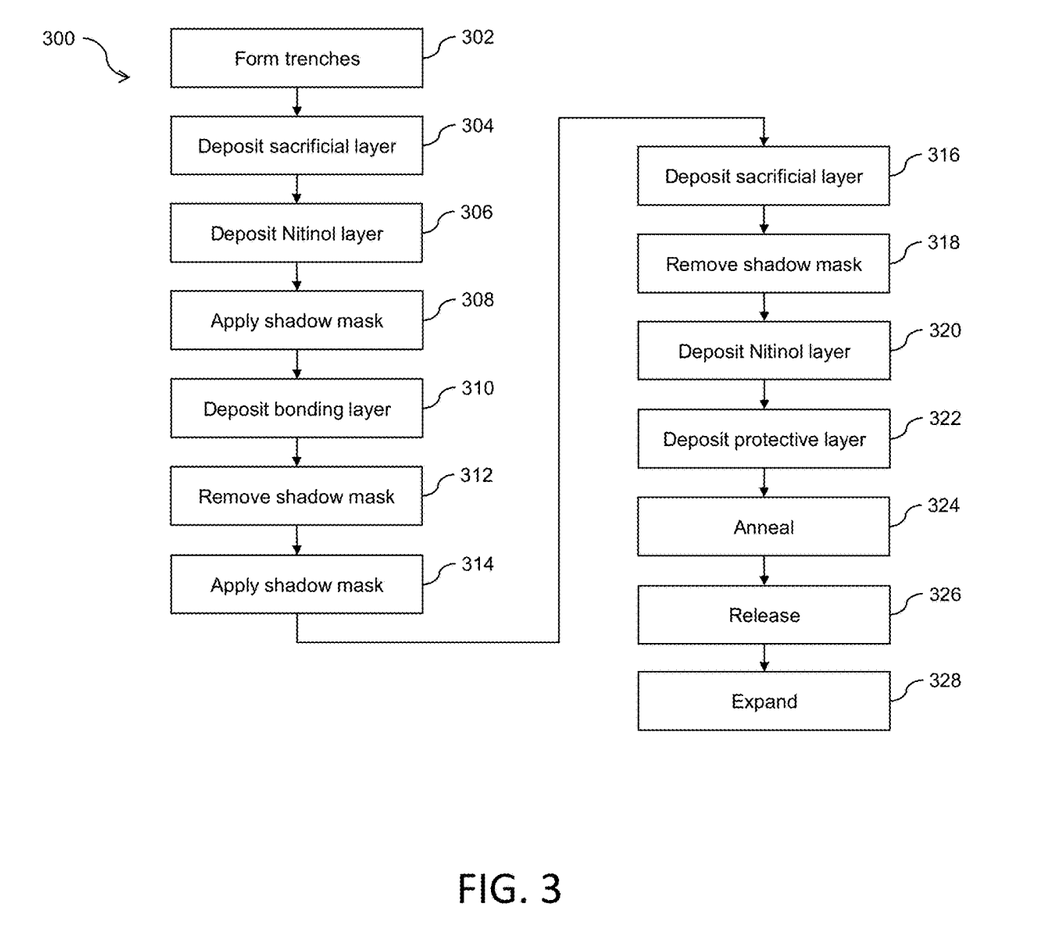
FIG. 3 is a flow diagram of a process to fabricate a thin-film micromesh for a medical device according to an embodiment.
Figure 4A:
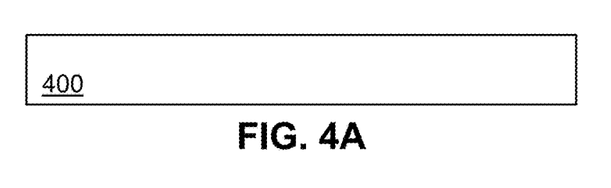
FIGS. 4A-Q are diagrammatic cross-sectional views of layers being formed on a substrate to fabricate a thin-film micromesh according to an embodiment.
Figure 4B:
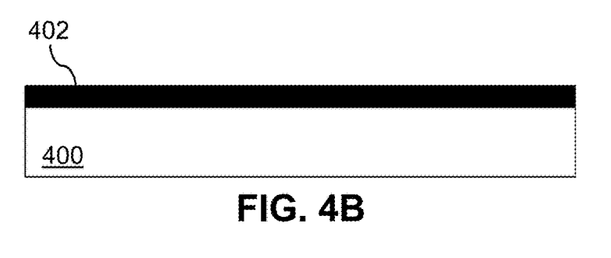
Figures 4C, 4D:
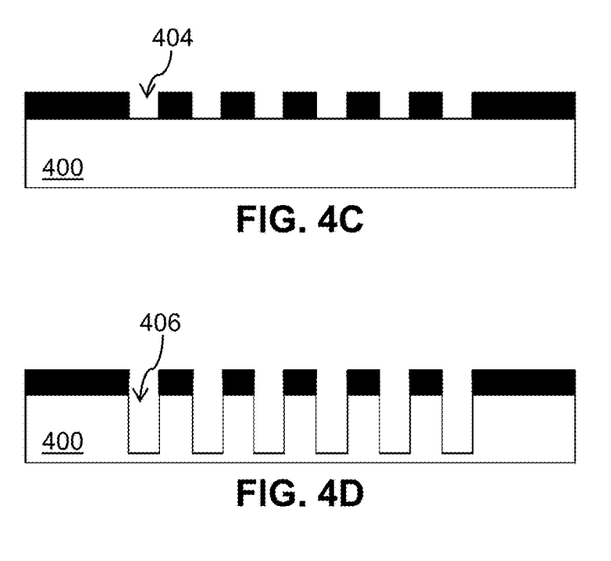
Figure 4E:
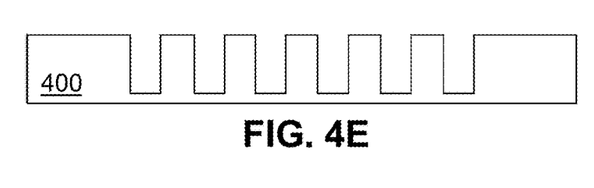
Figure 5A:
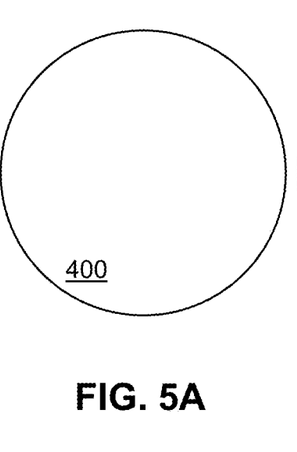
FIGS. 5A-H are diagrammatic top plan views of layers being formed on a substrate to fabricate a thin-film micromesh according to an embodiment.
Figure 5B:
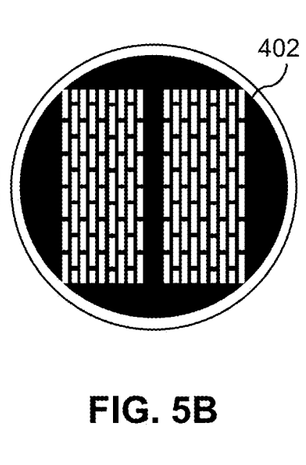
Figure 5C:
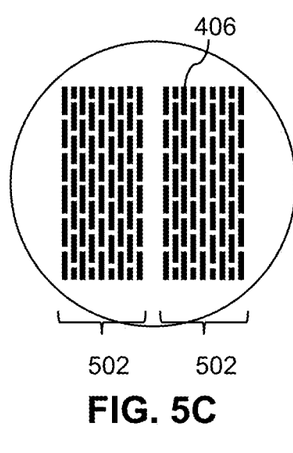

FIG. 3 is a flow diagram of a process 300 to fabricate a thin-film mesh, such as thin-film mesh 210 of FIGS. 2A-2G, for a thin-film mesh device, such as thin-film mesh device 220. At block 302, trenches are formed on a wafer 400 (e.g., a silicon wafer or other wafer) as shown in FIGS. 4A-4E and 5A-5C. FIGS. 4A and 5A show wafer 400, which may have an oxide layer with a thickness of between 500 nm and 1 µm on top. A photoresist 402 is spun-coated on wafer 400 as shown in FIG. 4B. By patterning and developing photoresist 402 using photolithography, a pattern of exposed areas 404 is formed as shown in FIG. 4C and FIG. 5B. The pattern may define rows and columns of angled slits 202. The pattern of exposed areas 404 is available for etching. Deep reactive ion etching (DRIE) is performed to form grooves or trenches 406 that are at least 15 µm deep (e.g., between 25 µm and 200 µm deep) as shown in FIG. 4D. Photoresist 402 is removed and wafer 400 is cleaned, resulting in etched wafer 400 with trenches 406 as shown in FIG. 4E and FIG. 5C. Trenches 406 may form a micropattern that provides a template for thin-film mesh 210. For example, the micropattern may define slits 202 in diagonal rows 225 and longitudinal columns 235, as shown in FIGS. 2A-2E. The resolution of the micropattern using the DRIE process may be, for example, approximately 1 µm. Although two micropatterns 502 for two thin-film meshes are shown in FIG. 5C, wafer 400 may include more micropatterns. The term "approximately," as used herein when referring to a measurable value, encompasses variations of ±20%, ±10%, ±5%, ±1%, ±0.5%, or ±0.1% of the value.

Figure 4F:
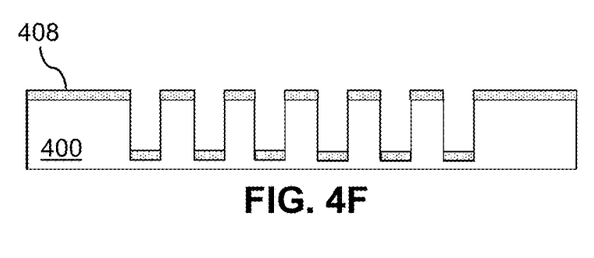

At block 304, a sacrificial layer 408 (e.g., a chrome sacrificial layer or a copper sacrificial layer), also referred to as a lift-off layer, is deposited as shown in FIG. 4F. Sacrificial layer 408 may be deposited by sputter deposition or evaporation deposition such as electron beam physical vapor deposition (EBPVD). Sacrificial layer 408 may have a thickness of, for example, 1 µm or less (e.g., approximately 500 nm).

Figures 4G, 4H:
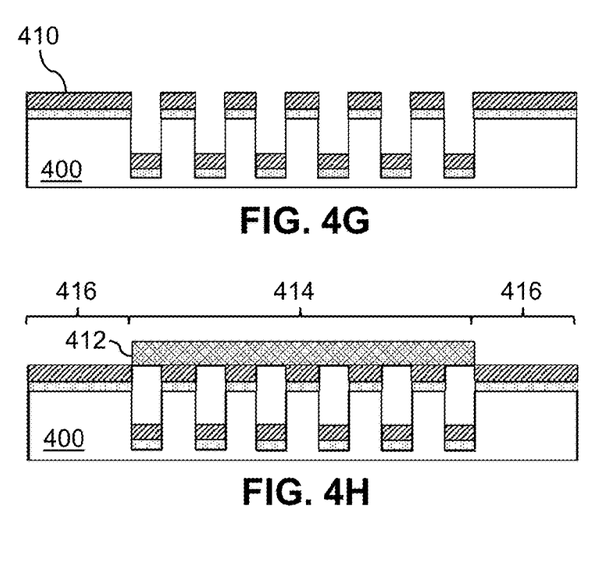
Figure 5D:
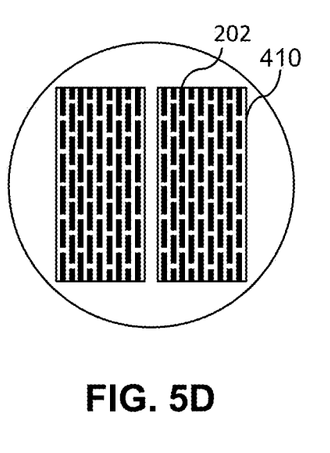

At block 306, a Nitinol layer 410 is deposited as shown in FIG. 4G and FIG. 5D. Nitinol layer 410 may have a thickness of, for example, between 1 µm and 20 µm (e.g., approximately 5 µm). As sputtered Nitinol at regions corresponding to trenches 406 fall to the bottom of trenches 406, the micropattern of trenches 406 of wafer 400 are duplicated on Nitinol layer 410 as corresponding fenestrations (e.g., closed fenestrations) such as slits 202 of thin-film mesh 210 as shown in FIGS. 2A-2E. The resulting pattern of fenestrations 202 may also be denoted as a fiche in that fenestrations 202 are in closed form prior to an expansion of thin-film mesh 210. Just like a microfiche, each fiche or pattern of fenestrations 202 effectively codes for resulting fenestrations when thin-film mesh 210 is expanded to fully open up fenestrations 202.

At block 308, a shadow mask 412 is applied as shown in FIG. 4H. Shadow mask 412 is applied to a mesh region 414 and exposes seam regions 416 for deposition of a bonding layer 418.

Figure 4I:
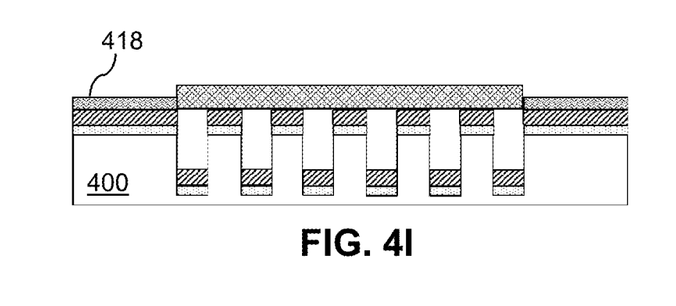

At block 310, bonding layer 418 (e.g., an aluminum bonding layer) is deposited as shown in FIG. 4I. Bonding layer 418 may have a thickness of, for example, 1 µm or less (e.g., approximately 500 nm).

Figure 4J:
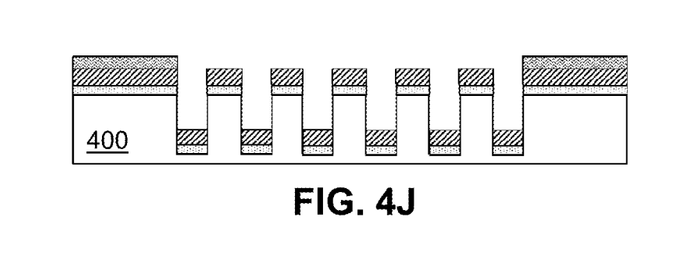

At block 312, shadow mask 412 is removed as shown in FIG. 4J.

Figure 4K:
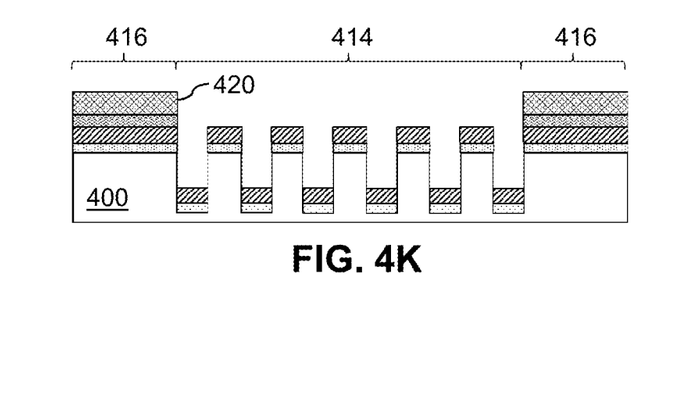

At block 314, a shadow mask 420 is applied as shown in FIG. 4K. Shadow mask 420 is applied to seam regions 416 and exposes mesh region 414 for deposition of a sacrificial layer 422.

Figure 4L:
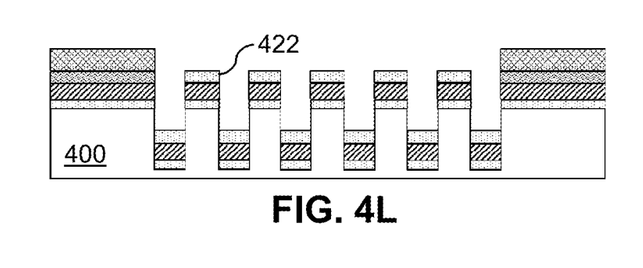
Figure 5E:
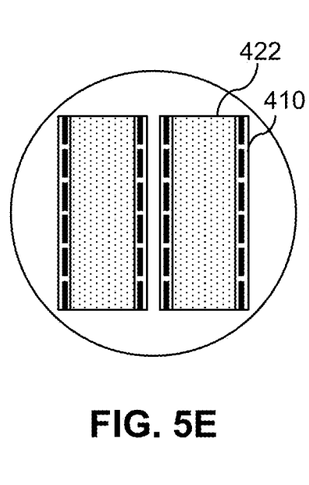

At block 316, sacrificial layer 422 (e.g., a chrome sacrificial layer or a copper sacrificial layer) is deposited as shown in FIG. 4L and FIG. 5E. Sacrificial layer 422 may have a thickness of, for example, 1 µm or less (e.g., approximately 500 nm).

Figure 4M:
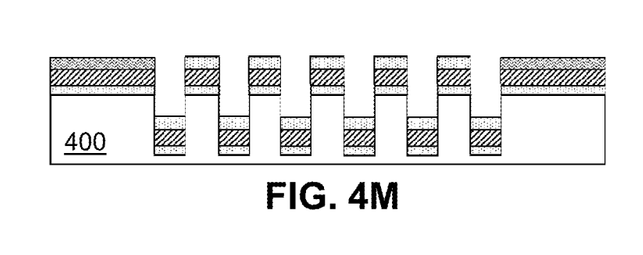

At block 318, shadow mask 420 is removed as shown in FIG. 4M.

Figure 4N:
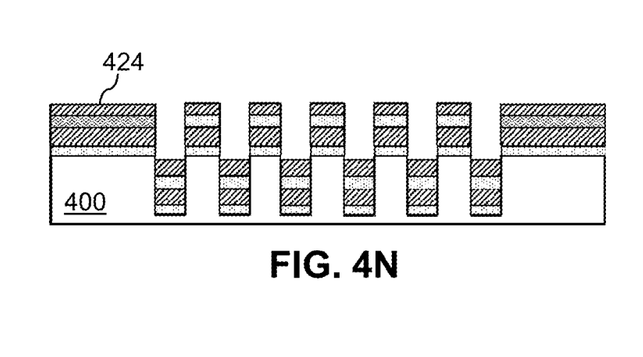
Figure 5F:
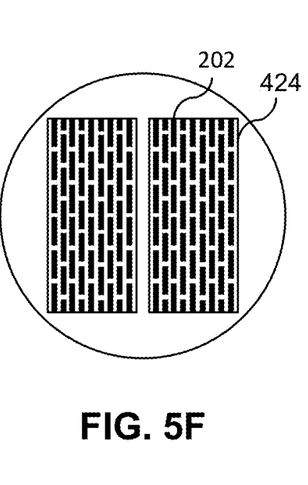

At block 320, a Nitinol layer 424 is deposited as shown in FIG. 4N and FIG. 5F. Nitinol layer 424 may have a thickness of, for example, between 1 µm and 50 µm (e.g., approximately 5 µm). Similarly to block 306, as sputtered Nitinol at regions corresponding to trenches 406 fall to the bottom of trenches 406, the micropattern of trenches 406 of wafer 400 are duplicated on Nitinol layer 424 as corresponding fenestrations (e.g., closed fenestrations) such as slits 202 of thin-film mesh 210 as shown in FIGS. 2A-2E.

Figure 4O:
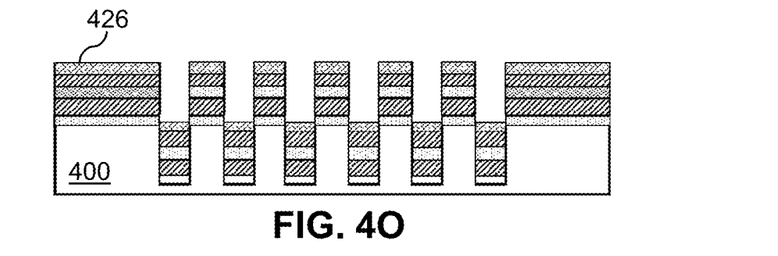

At block 322, a protective layer 426 (e.g., a protective chrome layer) is deposited as shown in FIG. 4O. Protective layer 426 may have a thickness of, for example, 1 µm or less (e.g., approximately 500 nm).

Figure 4P:
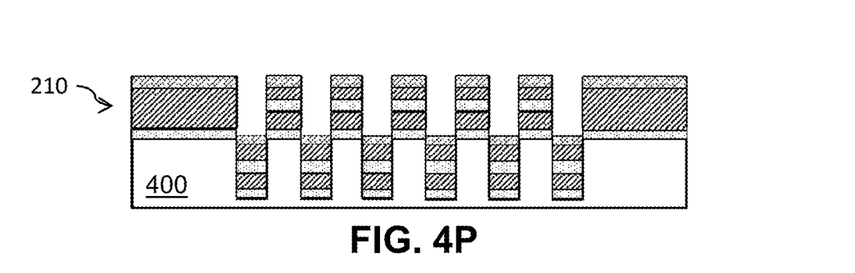

At block 324, Nitinol layers 410, 424 and bonding layer 418 are annealed to form thin-film mesh 210 as shown in FIG. 4P. Wafer 400 with Nitinol layers 410, 424 and bonding layer 414 may be annealed at a high temperature (e.g., approximately 675° C. for approximately 10 minutes) to melt bonding layer 418 and crystalize amorphous Nitinol layers 410, 424. Nitinol layer 410 and Nitinol layer 424 are fused in inseam region 416.

Figure 4Q:
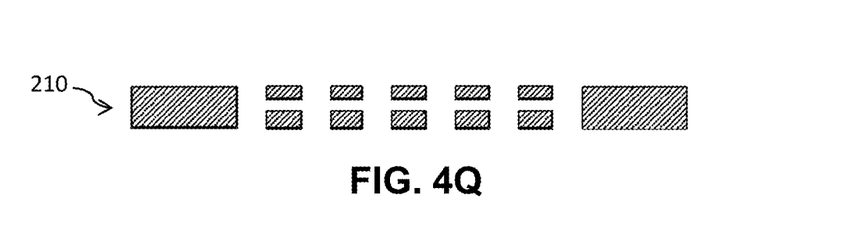
Figure 5G:
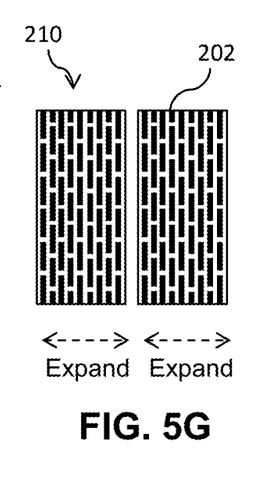

At block 326, thin-film mesh 210 is released as shown in FIG. 4Q and FIG. 5G. Annealed wafer 400 may be placed in chrome etchant (e.g., for approximately 1 hour) to release thin-film mesh 210 from top of the wafer 400.

Figure 5H:
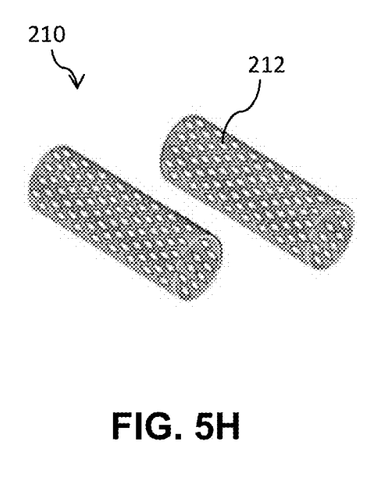

At block 328, thin-film mesh 210 is expanded to form a three-dimensional thin-film mesh 210 with angled fenestrations 202 that have been opened up such as a cylindrical tube as shown in FIG. 5H. It will be appreciated that combining the lift-off process with multiple-layer depositions of Nitinol separated by layers of sacrificial layers enables fabrication of thin-film meshes 210 of various other three-dimensional shapes in other embodiments.

A thin-film micro mesh membrane, or a corresponding hybrid membrane/structure may be used for various medical treatments as described below.

In some embodiments, a thin-film mesh membrane may be used at various treatment locations in a patient, such as in various types of neurovasculature, carotid vascular beds, cardiac vascular beds, aortic vascular beds, iliac vascular beds, renal vascular beds, peripheral vascular beds, upper extremity vascular beds, and other similar treatment locations.

In some embodiments, a thin-film mesh membrane, a thin-film mesh structure, or a corresponding hybrid membrane/structure may be used, for example, for to facilitate wound healing for burns, pressure ulcers, scar revisions, ischemic lower limb ulcers and other acute and chronic wounds.

In some embodiments, a thin-film mesh membrane, a thin-film mesh structure, or a corresponding hybrid membrane/structure may be used to stop acute bleeding whether from injury or from surgical intervention ("hemostasis").

In some embodiments, a thin-film mesh membrane, a thin-film mesh structure, or a corresponding hybrid membrane/structure may be used to facilitate bone healing that is wrapped around or placed within a fracture site, or is wrapped around structural elements formed of other materials (e.g. titanium) that bridge a gap between bones.

In some embodiments, a thin-film mesh membrane, a thin-film mesh structure, or a corresponding hybrid membrane/structure may be used to grow human chondrocytes and create a thin plate of cartilage. This cartilage plate could be used in joint operations to delay knee or hip replacement or other osteoarthritic conditions.

In some embodiments, a thin-film mesh membrane, a thin-film mesh structure, or a corresponding hybrid membrane/structure may be used to deliver chemotherapeutics directly to the site of a tumor following surgical excision of the tumor.

In some embodiments, a thin-film mesh membrane, a thin-film mesh structure, or a corresponding hybrid membrane/structure may be used in cardiac surgery to place cardiac myocytes at a site of myocardial infarction. Following infarct the surgeon would excise the scarred area and insert the membrane or the hybrid membrane to facilitate regrowth of healthy tissue as opposed to scar tissue that typically accompanies myocardial infarction.

In some embodiments, a thin-film mesh membrane, a thin-film mesh structure, or a corresponding hybrid membrane/structure may be used as a scaffold device for nerve regrowth following injury. The thin-film mesh membrane or hybrid membrane would have channels aligned like a native nerve to facilitate axon growth in a controlled manner.

In some embodiments, a thin-film mesh membrane, a thin-film mesh structure, or a corresponding hybrid membrane/structure may be used in reconstructive or cosmetic surgery to replace ligaments because of the elastic properties of thin-film mesh (e.g., breast tissue contains multiple small ligamentous elements that give rise to the shape and mechanical properties of the organ, and post-mastectomy prostheses, i.e., breast implants, are essentially non-structured bags of saline, silicone gel, or other materials).

In some embodiments, thin-film mesh membranes, thin-film mesh structures, and/or corresponding hybrid membranes/structures can be joined together to create the basis for more complex cartilaginous structures (e.g., external ear, portions of nose) when seeded with chondrocytes.

In some embodiments, a thin-film mesh membrane, a thin-film mesh structure, or a corresponding hybrid membrane/structure may be used to replace elements of the eye that have been injured traumatically or by disease (e.g., a tumor).

In some embodiments, a thin-film mesh membrane, a thin-film mesh structure, or a corresponding hybrid membrane/structure may be used to construct replacement elements of the bronchial tree in the lungs.

In some embodiments, a thin-film mesh membrane, a thin-film mesh structure, or a corresponding hybrid membrane/structure composed of or including Nitinol may be seeded with myocytes to construct replacement skeletal muscle. Because Nitinol has the ability to change shape when electrical current is passed through it, it may be advantageously be used in artificial limbs.

In some embodiments, a thin-film mesh membrane, a thin-film mesh structure, or a corresponding hybrid membrane/structure may be used as a means to deliver both small and large molecules (i.e. proteins) to anatomical sites of interest.

Embodiments described herein illustrate but do not limit the disclosure. It should also be understood that numerous modifications and variations are possible in accordance with the principles of the present disclosure. Accordingly, the scope of the disclosure is best defined only by the following claims.

What is claimed is:

1. A thin-film micromesh device comprising:
a backbone extending in a longitudinal axis; and
a thin-film micromesh assembled on the backbone, the thin-film micromesh comprising a plurality of slits elongated in a slit axis, wherein:
the slit axis is angled from the longitudinal axis,
the plurality of slits comprise a first type of slit elongated in a first slit axis forming a first angle with the longitudinal axis and a second type of slit elongated in a second slit axis forming a second angle with the longitudinal axis,
the first type of slit is provided in a first longitudinal column,
the second type of slit is provided in a second longitudinal column,
when the first type of slit and the second type of slit are expanded, the first type of slit and the second type of slit form pores, and
the pores formed from the first type of slit in the first longitudinal column are discrete from the pores of the second type of slit in the second longitudinal column.

2. The thin-film micromesh device of claim 1, wherein the plurality of slits are expandable in an expansion axis perpendicular to the slit axis.

3. The thin-film micromesh device of claim 1,
wherein the thin-film micromesh device has a cylindrical shape, and
wherein the plurality of slits are expanded such that the thin-film micromesh is expandable both along the longitudinal axis of the cylindrical shape thin-film micromesh and along a circumferential direction of the cylindrical shape thin-film micromesh.

4. The thin-film micromesh device of claim 3, wherein the thin-film micromesh is expandable along the circumferential direction allowing the cylindrical shape thin-film micromesh device to expand radially increasing a diameter of the cylindrical shape thin-film micromesh device.

5. The thin-film micromesh device of claim 3, wherein an angle formed between the slit axis and the longitudinal axis determines an expandability of the thin-film micromesh along the longitudinal axis relative to an expandability of the thin-film micromesh in the circumferential direction.

6. The thin-film micromesh device of claim 1, wherein the thin-film micromesh comprises thin-film Nitinol (TFN).

7. The thin-film micromesh device of claim 1, wherein the plurality of slits are arranged in series in a diagonal row parallel to the slit axis.

8. The thin-film micromesh device of claim 7, wherein diagonal rows of slits are arranged in parallel to form a longitudinal column of slits.

9. The thin-film micromesh device of claim 8, wherein a number of slits in the diagonal rows determines a force required to expand the thin-film micromesh.

10. The thin-film micromesh device of claim 1, wherein the first type of slit is a mirror image of the second type of slit with respect to the longitudinal axis.

11. The thin-film micromesh device of claim 1, wherein the first angle equals the second angle, but the first type of slit and the second type of slit are angled from the longitudinal axis in opposite directions.

12. The thin-film micromesh device of claim 1, wherein the first type slit is provided in a first longitudinal column and the second longitudinal column are separated by a third longitudinal column and a fourth longitudinal column.

13. The thin-film micromesh device of claim 12, wherein:
the third longitudinal column is formed from the first type of slit,
the fourth longitudinal column is formed from the second type of slit and is adjacent to the third longitudinal column, and
a V-shape is formed at an interface between the third longitudinal column and the fourth longitudinal column.

14. The thin-film micromesh device of claim 13. wherein an angle formed by the V-shape determines an expandability of the thin-film micromesh along the longitudinal axis relative to an expandability of the thin-film micromesh in the circumferential direction.

15. The thin-film micromesh device of claim 14, wherein increasing the angle formed by the V-shape increases the expandability of the thin-film micromesh along the longitudinal axis and decreases the expandability of the thin-film micromesh in the circumferential direction.

16. The thin-film micromesh device of claim 1, wherein the first longitudinal column and the second longitudinal column are arranged around the thin-film micromesh in an alternating matter, such that the first type of slit and the second type of slit form a zig-zag pattern around the thin-film micromesh.

17. The thin-film micromesh device of claim 16, wherein the first type of slit and the second type of slit are a mirror image of each other and the zig-zag pattern provides symmetrical or uniform expansion of the thin-film micromesh.

18. The thin-film micromesh device of claim 1, wherein the pores formed from the first type of slit and the pores formed from the second type of slit comprise diamond-shaped pores.

19. A method for forming the thin-film micromesh of claim 1, comprising:
deep reactive ion etching a micropattern of trenches on a surface of a substrate, the trenches corresponding to angled slits in the thin-film micromesh to be formed;
depositing a lift-off layer on the etched substrate;
depositing a first Nitinol layer over the lift-off layer; and
etching the lift-off layer to form the thin-film micromesh.

20. The method of claim 19, further comprising:
depositing a bonding layer on at least one area of the first Nitinol layer;
depositing a sacrificial layer on a remaining area of the first Nitinol layer;
depositing a second Nitinol layer on the bonding layer and the sacrificial layer; and
annealing the first Nitinol layer and the second Nitinol layer with the bonding layer;
wherein the etching further etches the sacrificial layer to form the thin-film micromesh having a three dimensional shape.

* * * * *

UNITED STATES PATENT AND TRADEMARK OFFICE
CERTIFICATE OF CORRECTION

PATENT NO. : 12,285,346 B2
APPLICATION NO. : 17/203349
DATED : April 29, 2025
INVENTOR(S) : Colin Kealey and Vikas Gupta

Page 1 of 1

It is certified that error appears in the above-identified patent and that said Letters Patent is hereby corrected as shown below:

In the Claims

Claim 12, Column 11, Lines 32-33, change "wherein the first type slit is provided in a first longitudinal column" to --wherein the first longitudinal column--.

Signed and Sealed this
Eighth Day of July, 2025

Coke Morgan Stewart
*Acting Director of the United States Patent and Trademark Office*